United States Patent
Serbousek et al.

(10) Patent No.: US 10,368,914 B2
(45) Date of Patent: Aug. 6, 2019

(54) FUSION SYSTEMS AND METHODS OF ASSEMBLY AND USE

(71) Applicant: IN QUEUE INNOVATIONS, LLC, Winona Lake, IN (US)

(72) Inventors: Jill A. Serbousek, Winona Lake, IN (US); Jeffrey Nycz, Warsaw, IN (US); Jon C. Serbousek, Winona Lake, IN (US)

(73) Assignee: IN QUEUE INNOVATIONS, LLC, Winona Lake, IN (US)

( * ) Notice: Subject to any disclaimer, the term of this patent is extended or adjusted under 35 U.S.C. 154(b) by 34 days.

(21) Appl. No.: 15/463,726

(22) Filed: Mar. 20, 2017

(65) Prior Publication Data
US 2017/0189070 A1 Jul. 6, 2017

Related U.S. Application Data

(63) Continuation of application No. PCT/US2015/051251, filed on Sep. 21, 2015.

(60) Provisional application No. 62/052,915, filed on Sep. 19, 2014.

(51) Int. Cl.
*A61B 17/70* (2006.01)
*A61B 17/88* (2006.01)
*A61B 17/00* (2006.01)

(52) U.S. Cl.
CPC ........ *A61B 17/7005* (2013.01); *A61B 17/701* (2013.01); *A61B 17/7002* (2013.01); *A61B 17/7004* (2013.01); *A61B 17/7085* (2013.01); *A61B 17/7091* (2013.01);
(Continued)

(58) Field of Classification Search
CPC ............ A61B 17/7005; A61B 17/7002; A61B 17/7004; A61B 17/701; A61B 17/7085; A61B 17/7091; A61B 17/888; A61B 17/8888; A61B 2017/00526
USPC ....... 606/264, 265, 266, 267, 270, 278, 279, 606/305, 308, 328, 99, 104
See application file for complete search history.

(56) References Cited

U.S. PATENT DOCUMENTS

| 5,057,109 | A | 10/1991 | Olerud |
| 5,540,688 | A | 7/1996 | Navas |
| 5,562,737 | A | 10/1996 | Graf |

(Continued)

FOREIGN PATENT DOCUMENTS

| WO | 2005072631 A1 | 8/2005 |
| WO | 2007149426 A2 | 12/2007 |

(Continued)

OTHER PUBLICATIONS

International Search Report and Written Opinion issued in PCT Application No. PCT/US2015/051251 dated Jan. 20, 2016.
(Continued)

*Primary Examiner* — Pedro Philogene
*Assistant Examiner* — David C Comstock
(74) *Attorney, Agent, or Firm* — Heslin Rothenberg Farley & Mesiti P.C.

(57) ABSTRACT

The present invention discloses fusion systems and methods of assembly and use. The fusion systems include a first fastener, a second fastener, and an elongate member with a first end and a second end. The first end being secured to the first fastener and the second end being secure to the second fastener. The method of assembling a fusion system and methods of using the fusion systems are also disclosed.

28 Claims, 15 Drawing Sheets

(52) U.S. Cl.
CPC ........ *A61B 17/888* (2013.01); *A61B 17/8888* (2013.01); *A61B 2017/00526* (2013.01)

(56) References Cited

U.S. PATENT DOCUMENTS

| | | | | |
|---|---|---|---|---|
| 8,377,099 | B1* | 2/2013 | Stauber | A61B 17/7004 606/261 |
| 2003/0100904 | A1* | 5/2003 | Biedermann | A61B 17/7032 606/272 |
| 2006/0241600 | A1* | 10/2006 | Ensign | A61B 17/7005 81/52 |
| 2007/0198014 | A1* | 8/2007 | Graf | A61B 17/7005 623/17.16 |
| 2008/0183214 | A1 | 7/2008 | Copp et al. | |
| 2009/0088799 | A1* | 4/2009 | Yeh | A61B 17/7005 606/246 |
| 2010/0228292 | A1* | 9/2010 | Arnold | A61B 17/7005 606/264 |
| 2012/0089191 | A1 | 4/2012 | Altarac et al. | |
| 2016/0278815 | A1* | 9/2016 | Fitzpatrick | A61B 17/7005 |

FOREIGN PATENT DOCUMENTS

| | | | |
|---|---|---|---|
| WO | 2008089298 | A2 | 7/2008 |
| WO | 2013169306 | A1 | 11/2013 |

OTHER PUBLICATIONS

Supplementary European Search Report and Annex issued for European Patent Application No. 15842936 and dated Jun. 12, 2018.

Extended European Search Report issued for European Patent Application No. 15841444.1 dated May 25, 2018.

* cited by examiner

FUSION SYSTEMS AND METHODS OF ASSEMBLY AND USE

CROSS REFERENCE TO RELATED APPLICATION

This application claims priority benefit from International Application No. PCT/US2015/051251 filed on Sep. 21, 2015, which claimed priority from U.S. provisional application No. 62/052,915 filed Sep. 19, 2014, each of which is incorporated herein by reference in its entirety.

FIELD OF THE INVENTION

The present invention relates generally to general surgery, orthopaedic and neurosurgical implants used for insertion within a patient's bones. More specifically, but not exclusively, the present invention concerns fusion and/or fixation systems for implantation into a patient's bones to maintain or re-establish proper spacing and alignment between or within the bones.

BACKGROUND OF THE INVENTION

Spinal deformities may result from disease, age, or trauma causing destabilization of the spine. To correct destabilization of a patient's spine, posterior fusion device systems may be used. The posterior fusion device systems that are currently available are designed to be applicable to single and multiple level stabilizations. Currently used pedicle or polyaxial screws use a top down locking mechanism that may allow for rod loosening and/or micro motion between the screws due to improper rod seating which may extend the time to achieve fusion or lead to non-fusion. The rod micro motion may be created by the use of a through slot in the screw to position the rod and the lack of a physical constraint on the end of the rod which is captured within the screw head locking mechanism. These fusion device systems and the instrumentation used for insertion into a patient's spine are extensive, complicated, and expensive. Further, additional bones in a patient's body may be fractured or otherwise damaged from disease, age or trauma and may require systems to maintain or re-establish proper alignment and positioning. Therefore, improved fusion and/or fixation device systems and instrumentation are needed.

SUMMARY OF THE INVENTION

Aspects of the present invention provide fusion and/or fixation systems and methods that can maintain or re-establish anatomic spacing within a patient's bones, for example, a patient's spine or bone fracture location.

In one aspect, provided here is a fusion system, including a first one piece screw, a second one piece screw, and a rod coupled to the first one piece screw at a first end and the second one piece screw at a second end, wherein the rod may be positioned at varying angulations with respect to the first and second one piece screws.

In another aspect, provided herein is a fusion system, including a first fastener, a second fastener, and an elongate member with a first end and a second end, wherein the first end is secured to the first fastener and the second end is secured to the second fastener.

In a further aspect, provided herein is a method for assembling a fusion system including: obtaining a first tower, a second tower, a first fastener, a second fastener, and an elongate member; coupling the first fastener to the first tower; coupling the second fastener to the second tower; inserting a first end of the elongate member into the first fastener; inserting a second end of the elongate member into the second fastener; coupling a first locking cap to a screwdriver; screwing the first locking cap into a head of the first fastener to secure the first end of the elongate member to the first fastener; coupling a second locking cap to a screwdriver; and screwing the second locking cap into a head of the second fastener to secure the second end of the elongate member to the second fastener.

In yet another aspect, provided herein is a surgical method for inserting a fusion system, including exposing a patient's vertebrae and obtaining the fusion system. The method may also include inserting a first fastener into a first vertebra and inserting a second fastener into a second vertebra adjacent to the first vertebra. Further, the method may include coupling the first fastener and second fastener.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion.

DETAILED DESCRIPTION FOR CARRYING OUT THE INVENTION

Generally stated, disclosed herein are fusion and/or fixation systems. Further, methods of assembling the fusion and/or fixation systems and surgical methods for inserting the fusion and/or fixation systems are discussed.

In this detailed description and the following claims, the words proximal, distal, anterior, posterior, medial, lateral, superior, inferior, cephalad and caudally are defined by their standard usage for indicating a particular part of a bone or implant according to the relative disposition of the natural bone or directional terms of reference. For example, "proximal" means the portion of an implant nearest the insertion instrument, while "distal" indicates the portion of the implant farthest from the insertion instrument. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure, "cephalad" means a direction toward the head and "caudally" means a direction toward the inferior part of the body.

Figure 1:
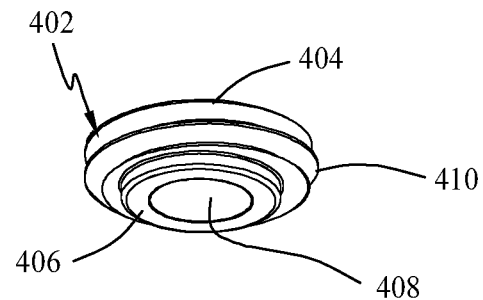
FIG. 1 is a perspective view of a bottom of a set screw and the base of a fastener of a fusion system, in accordance with an aspect of the present invention.
Figure 2:
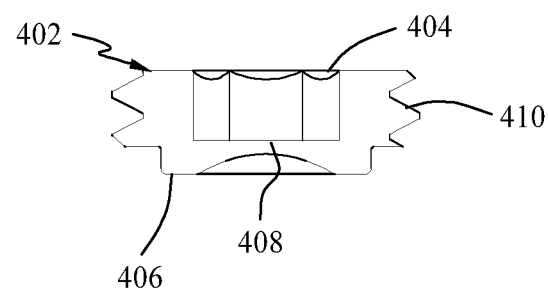
FIG. 2 is a side view of a cross section of a set screw and the base of a fastener of a fusion system, in accordance with an aspect of the present invention.
Figure 5:
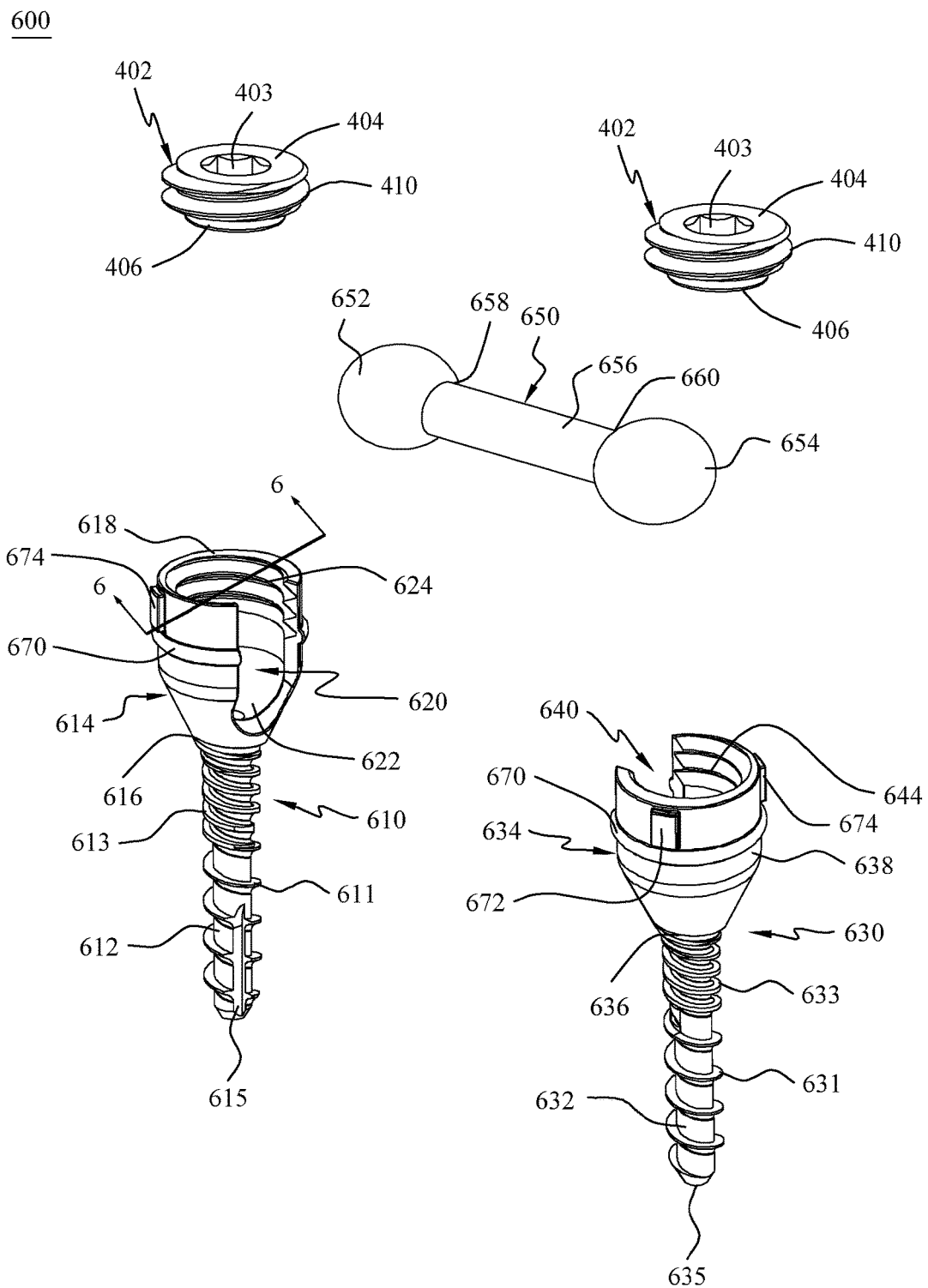
FIG. 5 is a partially exploded perspective view of another embodiment of a fusion system, in accordance with an aspect of the present invention.
Figure 15:
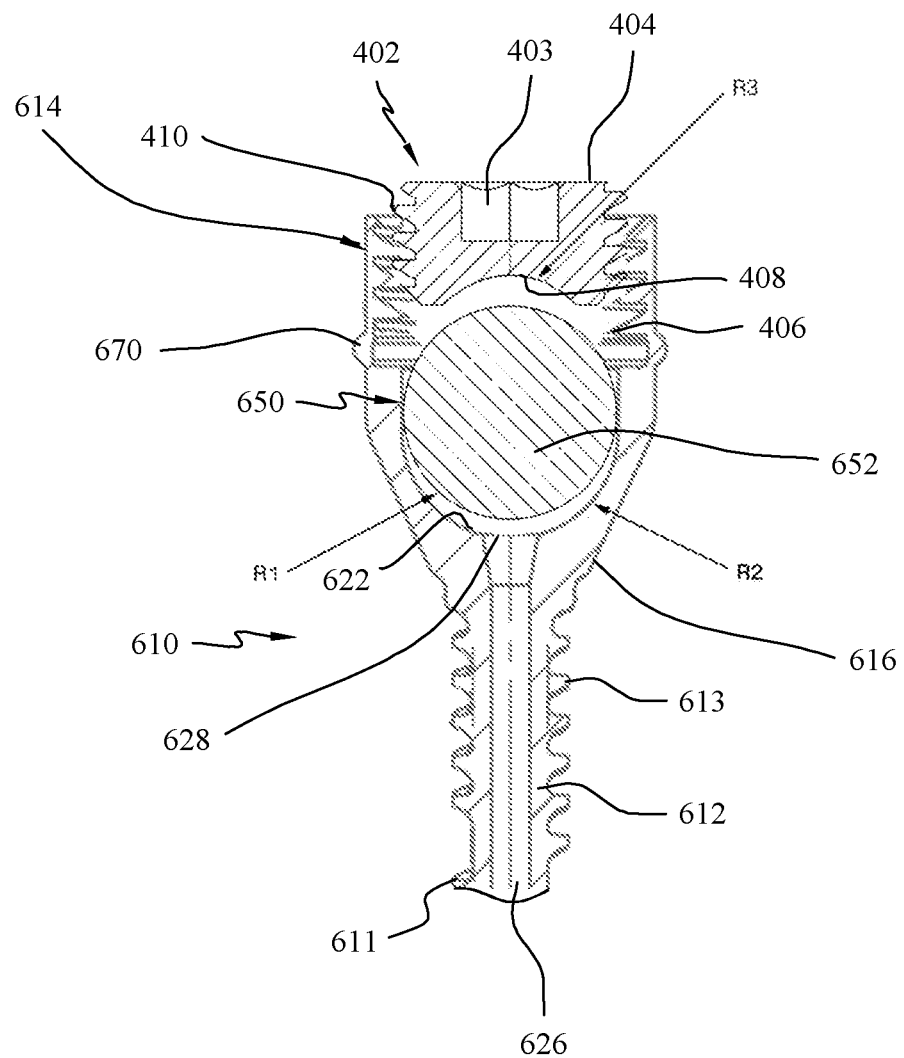
FIG. 15 is a cross-sectional view of a portion of the assembled fusion system of FIG. 5, in accordance with an aspect of the present invention.

Referring now to FIGS. 1, 2 and 5, a set screw 400 is shown. The set screw or locking cap 400 may include a top surface 404 and a bottom surface 406. The top surface 406 may include an opening 403 for receiving a screwdriver. The bottom surface 406 may include a recess 408. The recess 408 may include a radius R3, as shown in FIG. 15, and described in greater detail below. The set screw 400 may also include threads 410 on the exterior surface of the set screw 400 between the top surface 404 and the bottom surface 406. For example, the set screw 400 may be used with elongate members 550, 650 which each include ball ends 552, 554, 652, 654 that would be received within the recess 408 on the bottom surface 406 of the set screws 400.

Figures 3, 4:
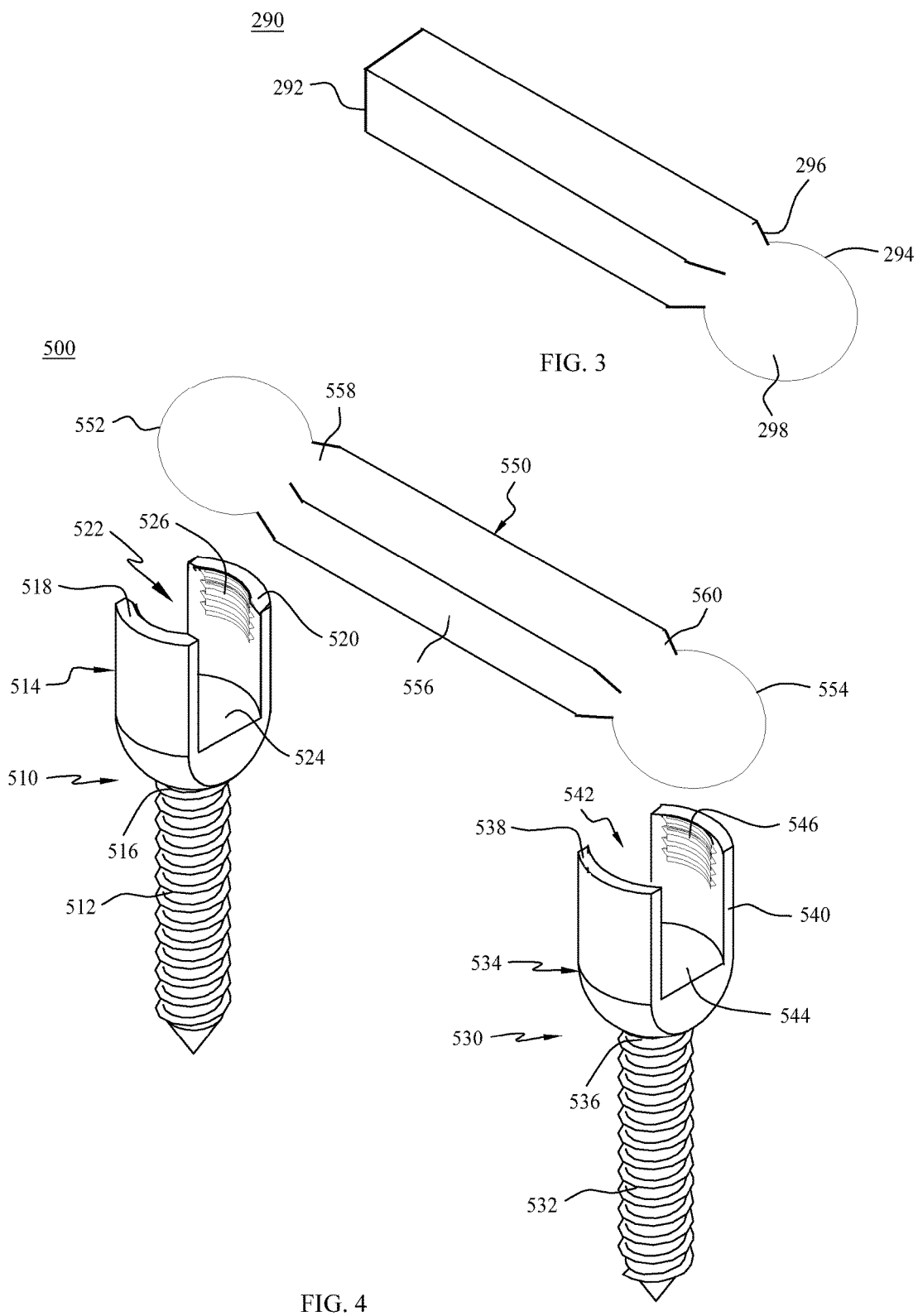
FIG. 3 is a perspective view of an elongate member for a fusion system, in accordance with an aspect of the present invention.
FIG. 4 is a partially exploded perspective view of a fusion system, in accordance with an aspect of the present invention.

FIG. 3 shows an embodiment of an elongate member 290. The elongate member 290 includes a first end 292 and a second end 294. The first end 292 has a rectangular shape which angles at a tapered portion 296 to the second end 294 which is a ball end 298. The second end 294 may have a diameter larger than the diameter of the tapered portion 296 and the body of the rod. The elongate member 290 may be used with, for example, a first fastener assembly 510 to receive the first end 292 and a second fastener 530 to receive the second end 294 or vice versa, as described in greater detail below.

As shown in FIG. 4, a fusion and/or fixation system 500 may include a first fastener 510, a second fastener 530, and an elongated member 550. The first fastener 510 may include a shaft 512, a head 514, and a neck 516 connecting the shaft 512 and head 514. The shaft 512 may be threaded, for example, along its entire length or along only a portion of the length or alternatively, the shaft 512 may be non-threaded. The head 514 may include a first arm 518, a second arm 520, and a passageway 522 extending between the first arm 518 and the second arm 520. The first arm 518 and second arm 520 each have an interior surface formed by the passageway 522. The passageway 522 creates two openings separating the first arm 518 and the second arm 520. The openings of the passageway 522 are sized to allow a center portion 556 of the elongate member 550 or the first end 292 of the elongate member 290 to pass through the openings, but not the ball ends 294, 552, 554 of the elongate members 290, 550, respectively. The passageway 522 also forms a base 524 near the bottom of the head 514. The base 524 may be, for example, planar as illustrated, alternatively, the base 524 may be curved or arced to correspond to the shape of the first end 552 of the rod 550. For example, the base 524 may be concave. The first arm 518 and the second arm 520 may each be curved to form a rounded passageway 522 for receiving the rod 550. In addition, the first arm 518 and the second arm 520 may have, for example, a threaded portion 526 that extends along at least a portion of the interior surface of each of the first and second arms 518, 520 from a top surface of the head 514 toward the base 524. The threaded portion 526 may receive a locking mechanism (not shown), such as, set screw 400, to secure the elongate member 550 to the first fastener 510. The locking mechanism (not shown) may have a bottom surface that is dimensioned to couple to the rounded end 552 of the elongate member 550. Thus, the bottom surface of the locking mechanism may be, for example, concave. Alternatively, the locking mechanism may be, for example, a press fit mechanism to secure the elongate member 550 to the heads 514, 534 of the fasteners 510, 530.

With continued reference to FIG. 4, the second fastener 530 may include a shaft 532, a head 534, and a neck 536 connecting the shaft 532 and head 534. The shaft 532 may be threaded, for example, along its entire length or along only a portion of the length, or alternatively, the shaft 532 may be non-threaded. The head 534 may include a first arm 538, a second arm 540, and a passageway 542 extending between the first arm 538 and the second arm 540. The first arm 538 and the second arm 540 each have an interior surface formed by the passageway 542. The passageway 542 also forms a base 544 near the bottom of the head 534. The base 544 may be, for example, planar as illustrated, alternatively, the base 544 may be curved or arced to correspond to the rounded shape of the rod 550. The first arm 538 and the second arm 540 may each be curved to form a rounded passageway 542 for receiving the rod 550. In addition, the first arm 538 and the second arm 540 may have, for example, a threaded portion 546 that extends along at least a portion of the interior surface of each of the first and second arms 538, 540 from a top surface of the head 534 toward the base 544. The threaded portion 546 may receive a locking mechanism (not shown) to secure the elongate member 550 to the second fastener 530, for example, set screw 400. The locking mechanism (not shown) may have a bottom surface that is dimensioned to couple to the rounded end 554 of the elongate member 550. Thus, the bottom surface of the locking mechanism may be, for example, concave.

The elongate member 550, as shown in FIG. 4, may include a first end 552, a second end 554, and a center portion 556 extending between the first end 552 and second end 554. The first end 552 and second end 554 may be rounded to correspond to the rounded passageways 522, 542 of the first and second fasteners 510, 530, respectively. The center portion 556 may be, for example, smaller than the first end 552 and the second end 554. For example, the center portion 556 may have a width that is smaller than the diameter of the first and second ends 552, 554. The elongate member 550 may also include a first tapered portion 558 coupling the center portion 556 to the first end 552 and a second tapered portion 560 coupling the center portion 556 to the second end 554. The first tapered portion 558 and the second tapered portion 560 may have a smaller dimension than the first end 552 and second end 554, respectively.

Figure 6:
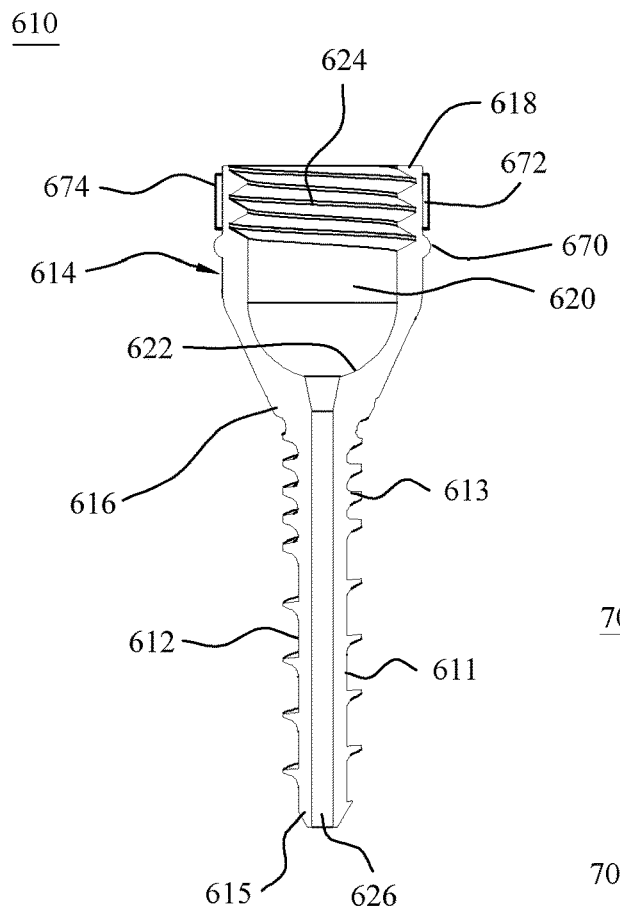
FIG. 6 is a cross-section of a fastener of the fusion system of FIG. 5 taken along line 6-6, in accordance with an aspect of the present invention.

Another fusion and/or fixation system 600 is shown in FIG. 5 and may include a first fastener 610, a second fastener 630, an elongated member 650, and two locking members or caps 400. As shown in FIGS. 5-6 the first fastener 610 may include a shaft 612, a head 614, and a neck 616 connecting the shaft 612 and head 614. The shaft 612 may be threaded, for example, along its entire length or along only a portion of the length, alternatively, the shaft 612 may also be non-threaded. As depicted in FIGS. 5 and 6, the shaft 612 may include varying thread configurations along the shaft 612 length, for example, the shaft 612 may include a single lead thread 611 at the distal end of the shaft 612 and a dual lead thread 613 at the proximal end of the shaft 612. The dual lead thread 613 provides increased bone contact within the cortical margin to increase fastener 610 stability. The dual lead thread 613 may extend into the tapered neck 616 of the fastener 610 to provide additional cortical bone purchase and allow for potential bone ingrowth into the thread form for increased fixation. The shaft 612 may also include a leading tip 615. The leading tip 615 may include, for example, a sharp cutting edge to assist with inserting the fastener 610 into the bone, which may eliminate the need for tapping into the bone prior to implantation of the fastener 610.

Figure 16:
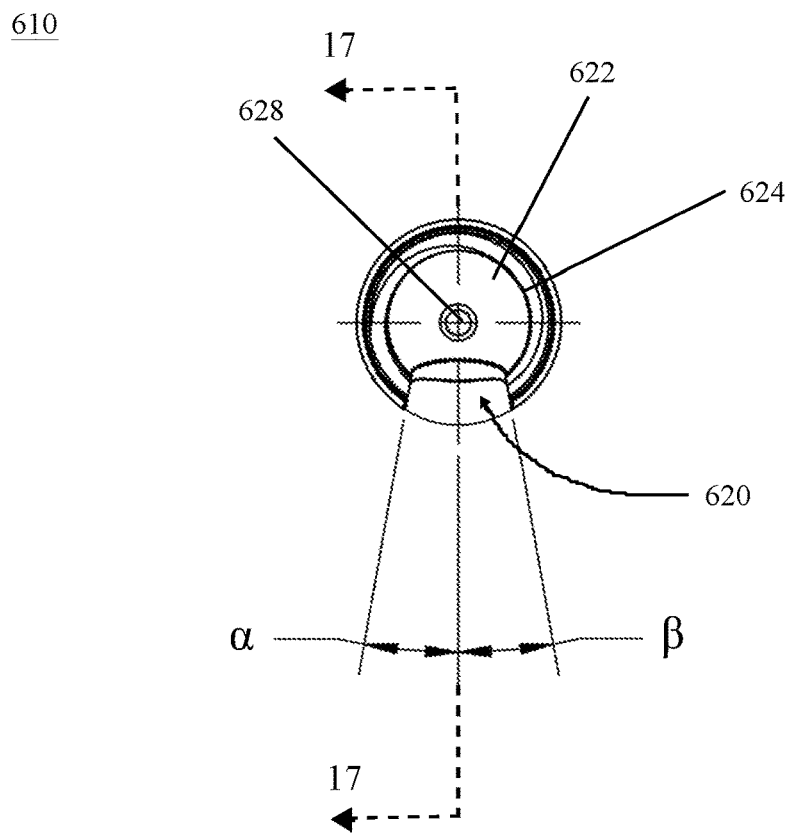
FIG. 16 is a top view of a fastener of the fusion system of FIG. 5, in accordance with an aspect of the present invention.
Figure 17:
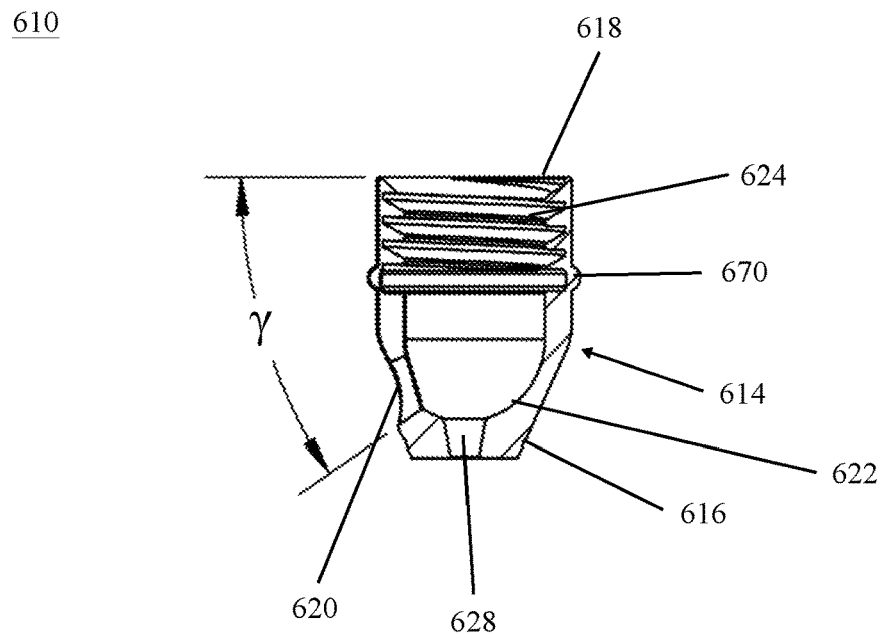
FIG. 17 is a side cross-sectional view of a portion of fastener of the fusion system of FIG. 5 taken along line 17-17 in FIG. 16, in accordance with an aspect of the present invention.

With continued reference to FIGS. 5 and 6, the head 614 may include a body 618 with an opening or slot 620 extending into the body 618 from the top of the head 614 and a portion of the body 618. The body 618 may be curved and may extend, for example, circumferentially greater than 180° and less than 345° leaving an opening 620 of, for example, greater than 15° and less than 180°, and more preferably may be curved and may extend, for example, circumferentially approximately 270° leaving an opening 620 of, for example, approximately 90°. The opening 620 may extend from the top surface of the head 614 down to a position below the midline of the head 620. The body 618 only, including one opening 620 provides additional support for the rod 650 to prevent longitudinal movement of the rod 650 after insertion into the patient. The opening 620 is shaped to provide for rod translation in both the axial plane, i.e. up and down direction, and the rotational plane, i.e. left and right direction. The opening 620 may also be shaped to allow for rotation of the head 614 of the fastener 610 about the multi-axis of the first end 652 or the rod 650. In one embodiment, as shown in FIGS. 16 and 17, the opening 620 allows for, for example, an angle $\gamma$ of rod positioning in the axial plane and an included angle $\alpha$, $\beta$ of rod positioning in the rotational plane. For example, $\gamma$ may range from approximately 5° to 75° and more preferably from approximately 20° to 40°, $\alpha$ may range from approximately 1° to 70° and more preferably from approximately 5° to 15°, and $\beta$ may range from approximately 1° to 70° and more preferably from approximately 5° to 15°. In one embodiment, for example, $\gamma$ may be approximately 34°, $\alpha$ may be approximately 10°, and $\beta$ may be approximately 10°. The opening 620 allows for rod angulation and/or positioning that provides for anatomic variability of the rod 650 when inserted into the fastener 610, while capturing the ball end 652 to maintain the distance between the first fastener 610 and the second fastener 630. The anatomic variability enables the rod 650 to be implanted into a patient at an angle when desirable for correction. The thickness of the rod 650 may also be altered to provide for a larger or smaller angle for the desired correction. The body 618 may have an interior surface formed by the opening 620.

The opening 620 also forms a base 622 near the bottom of the head 614, as shown in FIGS. 5 and 6. The base 622 may be, for example, curved or arced to match the shape of the first end 652 of the rod 650 as illustrated, alternatively the base 622 may be planar. The body 618 may be curved to receive the rounded end of the rod 650. In addition, the body 618 may have, for example, a threaded portion 624 that extends along at least a portion of the interior surface of the body 618 from a top surface of the head 614 towards the base 622. The threaded portion 624 may receive a locking mechanism to secure the elongate member 650 to the first fastener 610, such as, set screw or locking cap 400. The locking mechanism 400 may have a recess 408 that is shaped to receive the rounded end 652 of the elongate member 650. For example, the recess 408 of the set screw 400 may be dimensioned to be smaller than the first end 652 of the elongate member 650. Thus, the bottom surface of the locking mechanism may be, for example, concave. The head 614 may also include a ridge 670 extending around the exterior surface of the head 614. The head 614 may further include a first tab 672 and a second tab 674 on the exterior surface of the head 614 and positioned between the top of the fastener 610 and the ridge 670.

As shown in FIG. 5, the second fastener 630 may be of the type described above with reference to first fastener 610. The second fastener 630 may include a shaft 632, a head 634 with a body 638, an opening 640, a base (not shown) and a threaded portion 644, and a neck 636 extending between the head 634 and shaft 632, which may be of the type described above with reference to the shaft 612, head 614 with the body 618, an opening 620, a base 622 and a threaded portion 624, and a neck 616 which will not be described again here for brevity sake. A locking mechanism, such as, set screw 400, may also be used with the second fastener 630 for insertion into the head 634 to engage the threaded portion 644. The locking mechanism 400 may be used to secure the elongate member 650 to the second fastener 630. The locking mechanism 400 may include a recess 408 that is shaped to correspond to the rounded end 654 of the elongate member 650. The recess 408 in the locking mechanism 400 may have a curvature dimensioned to be smaller than the curvature of the rounded end 654 to secure the rounded end 654 in the head 634 of the fastener 630. Alternatively, the locking mechanism may be, for example, a press fit mechanism to secure the elongate member 650 to the heads 614, 634 of the fasteners 610, 630. Once both locking mechanisms 400 are secured in the fasteners 610, 630, the distance between the fasteners 610, 630 is secured.

The elongate member or rod 650, as shown in FIG. 5, may include a first end 652, a second end 654, and a shaft portion 656 extending between the first end 652 and second end 654. The first end 652 and second end 654 may be rounded or ball ends with shapes to correspond to the rounded openings 620, 640 of the first and second fasteners 610, 630, respectively. The ball ends 652, 654 may be sized such that they have a diameter larger than the diameter of the shaft portion 656, as well as, the recess 408 of the set screw 400 and the base 622 of the fasteners 610, 630, as shown in FIG. 15. The ball ends 652, 654 may have, for example, highly roughened or textured surfaces. The textured surfaces of the ball ends 652, 654 may assist with securing the elongate member 650 between the fasteners 610, 630 and the set screws 400. The roughened or textured surface may be of the type to allow for deformation of the roughened or textured surface when the set screw 400 is tightened into the head 614, 634 of the fastener 610, 630. The elongate member 650 may also include a first connection portion 658 coupling the center portion 656 to the first end 652 and a second connection portion 660 coupling the center portion 656 to the second end 654.

The fasteners 510, 530, 610, and 630 may be cannulated through the center of the shaft along a longitudinal axis of the fasteners 510, 530, 610, and 630 and include an opening, for example, opening 626 of fastener 610, as shown in FIG. 6, to enable insertion over a guide wire, k-wire, pin, or the like to assist with insertion into the patient. As shown in FIG. 6, the base 622 of the fastener 610 may include a screw engagement portion 628 positioned at the top of the opening 626. The screw engagement portion 628 may be shaped to correspond to the screwdriver instrument, such as screwdriver 800 described in greater detail below, for insertion of the fasteners 510, 530, 610, 630. The screw engagement portion 628 may have, for example, a female cylindrical, hexagon, or other polygonal shape.

Figure 7:
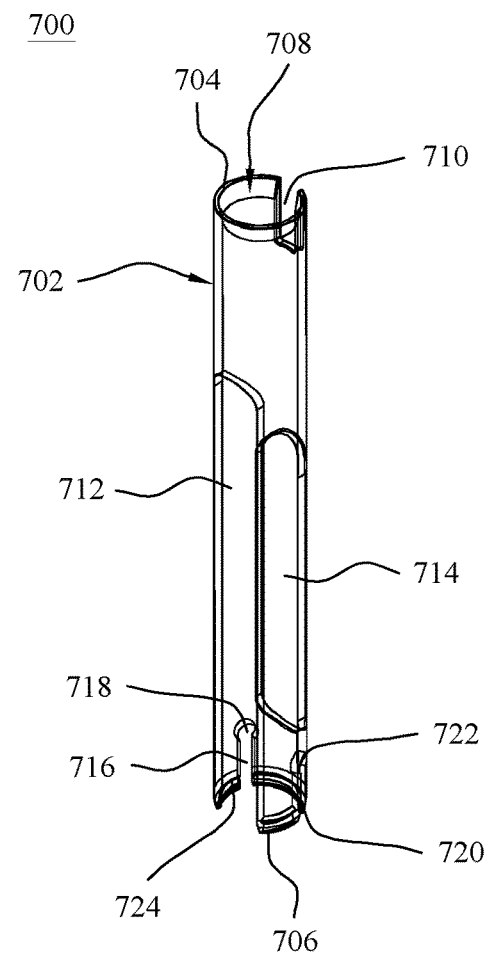
FIG. 7 is a perspective transparent view of an insertion tower, in accordance with an aspect of the present invention.
Figure 8:
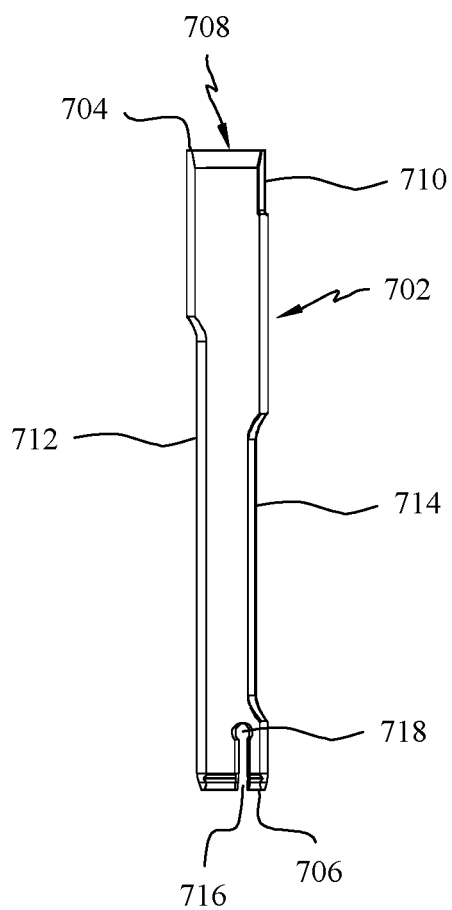
FIG. 8 is a side transparent view of the insertion tower of FIG. 7, in accordance with an aspect of the present invention.
Figure 9:
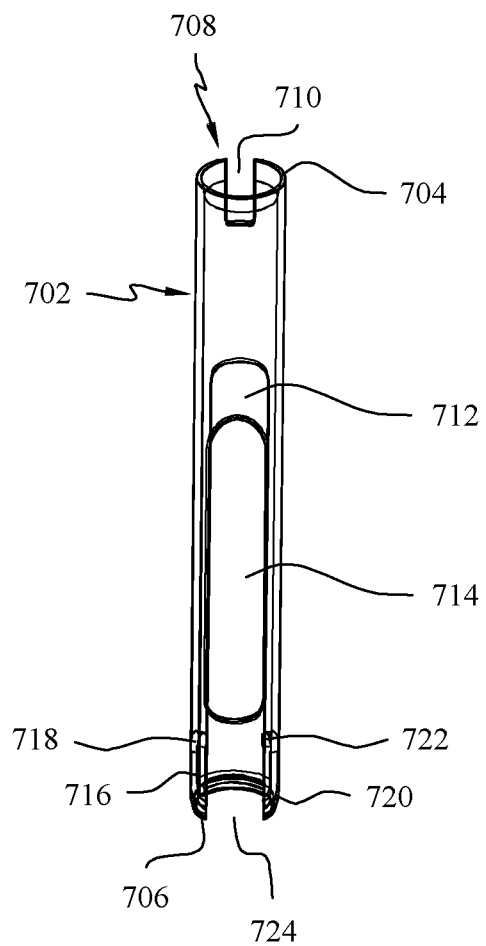
FIG. 9 is a front perspective transparent view of the insertion tower of FIG. 8, in accordance with an aspect of the present invention.
Figure 10:
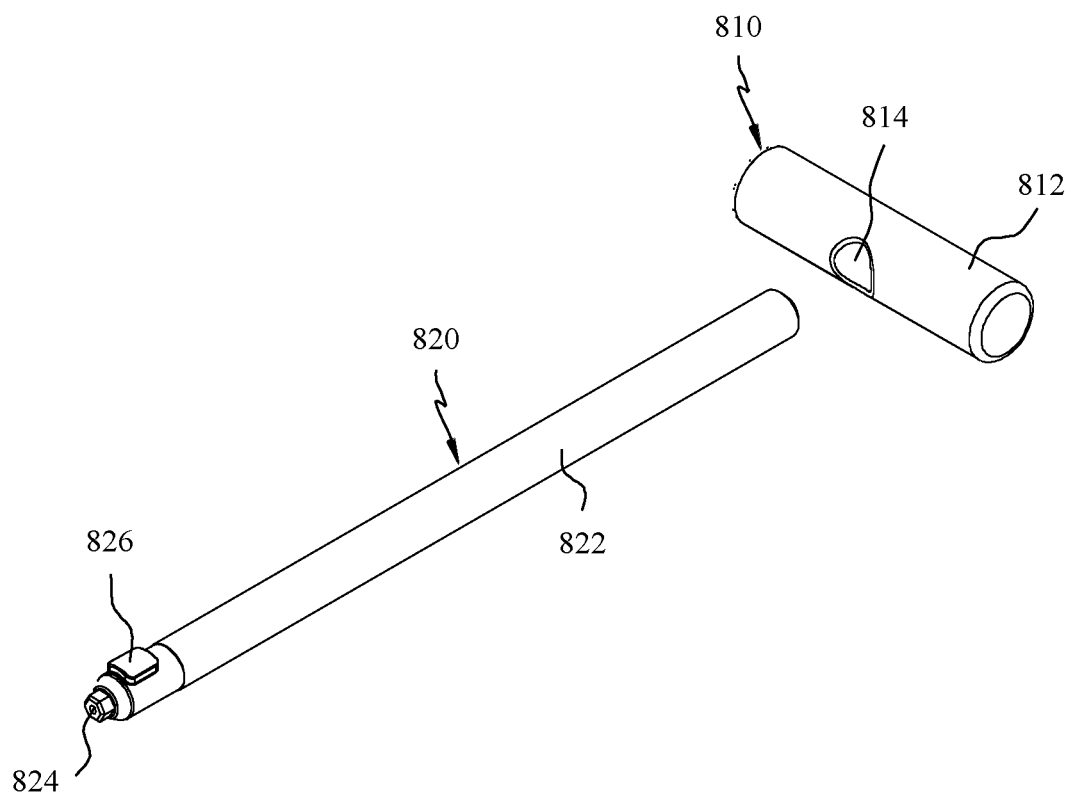
FIG. 10 is an exploded, perspective view of a screwdriver, in accordance with an aspect of the present invention.
Figure 11:
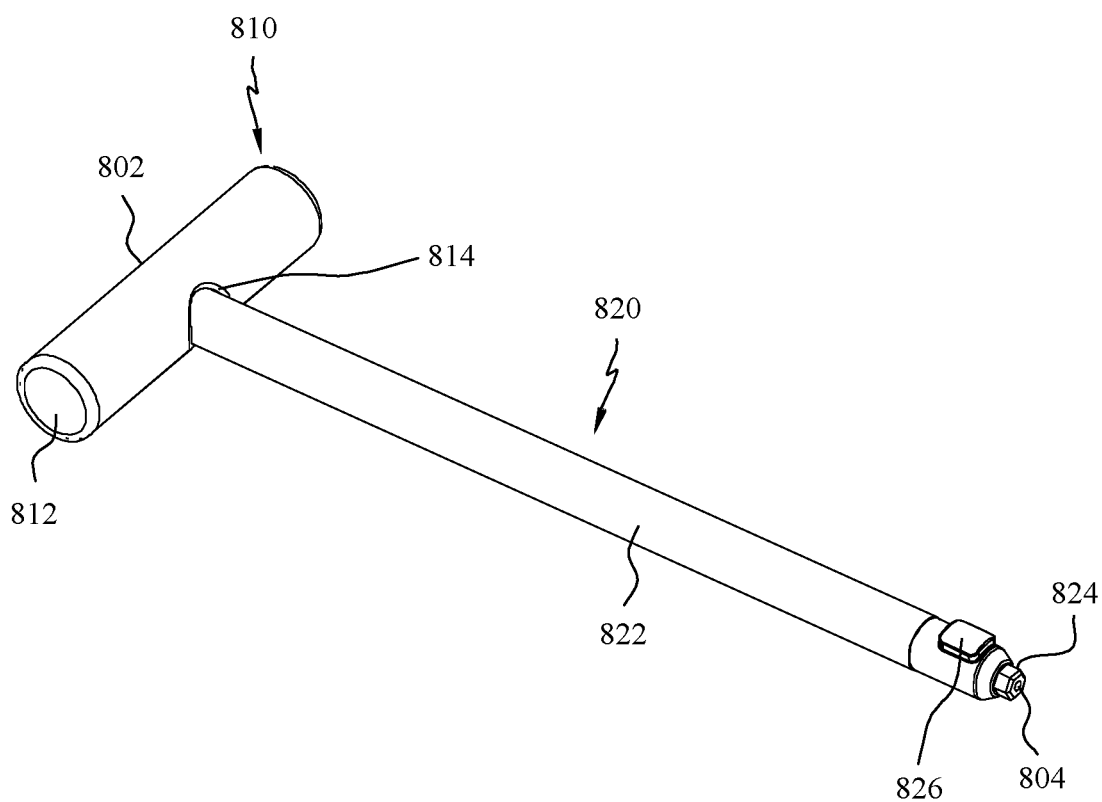
FIG. 11 is an assembled, perspective view of the screwdriver of FIG. 10, in accordance with an aspect of the present invention.
Figure 12:
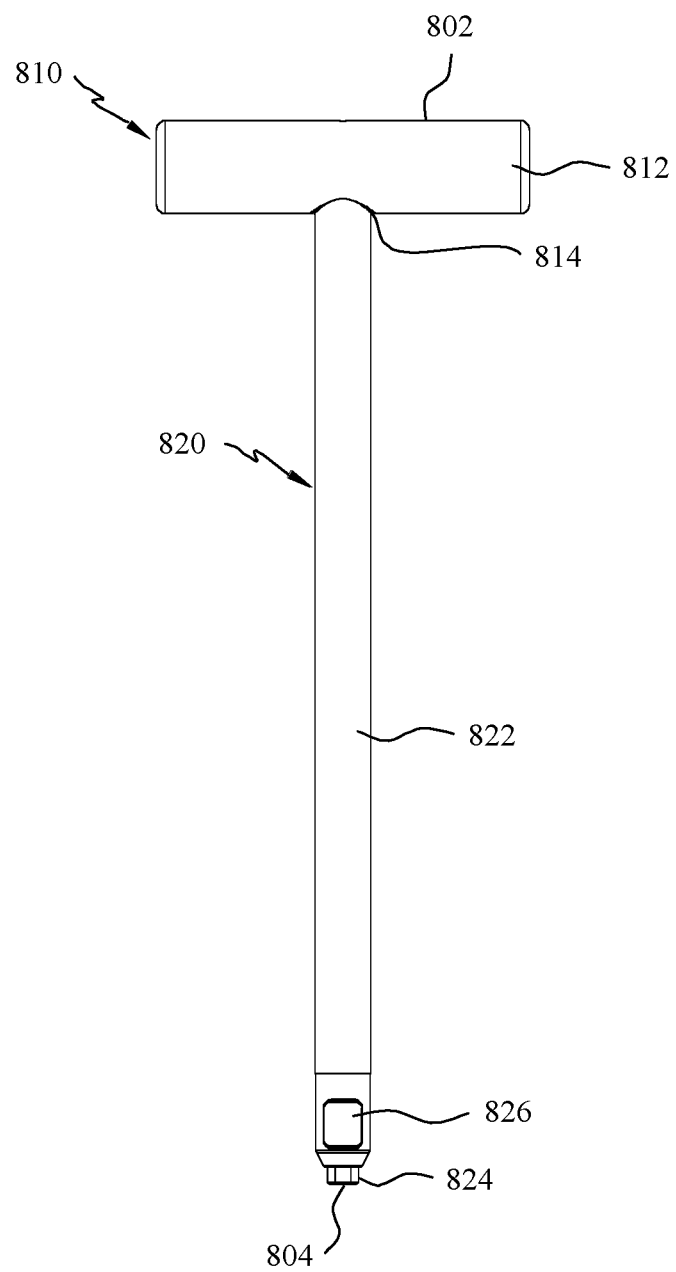
FIG. 12 is a side view of the screwdriver of FIG. 11, in accordance with an aspect of the present invention.
Figure 13:
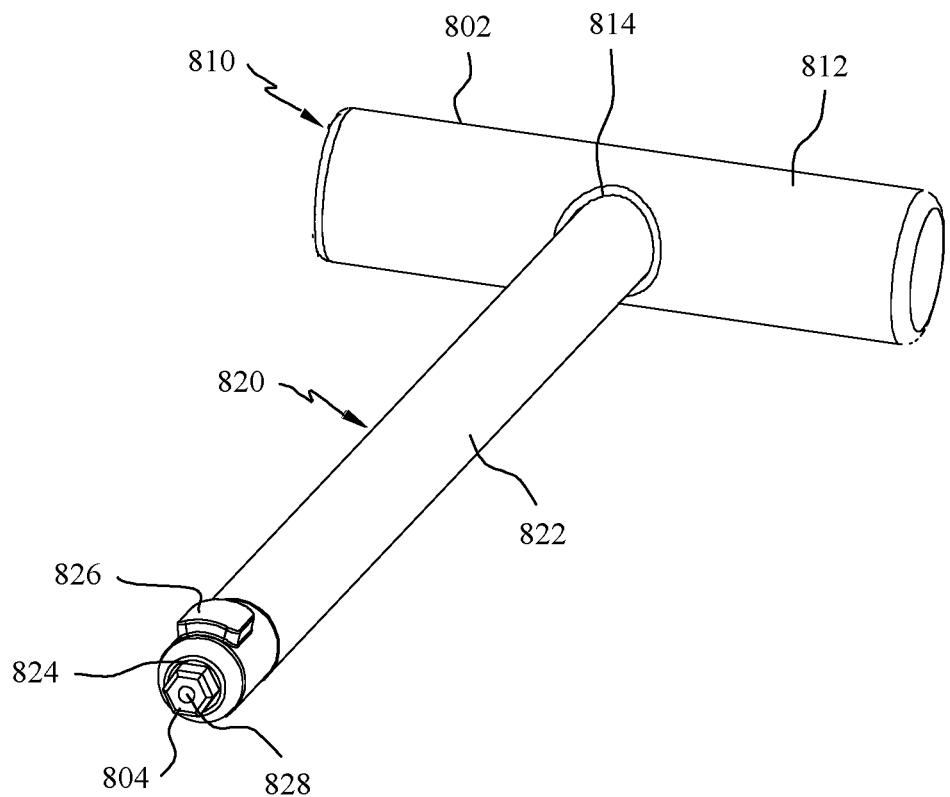
FIG. 13 is a first end view of the screwdriver of FIG. 12, in accordance with an aspect of the present invention.

A system for inserting the device 600 may include an insertion tower or tube 700, as shown in FIGS. 7-9, a screwdriver 800, as shown in FIGS. 10-13, and two fastener systems 610, 630. The insertion tower 700 may have a body 702 with a first end 704 and a second end 706. The body 702 may have a central opening 708 through the center of the body 702 along the longitudinal axis. The body 702 may also include a cutout 710 at the first end 704 of the body 702 extending from an exterior surface to an interior surface of the body 702. The body 702 may further include a channel 712 extending from the second end 706 of the body 702 toward the first end 704 and an opening 714 positioned opposite the channel 712. The channel 712 and opening 714 each extend from the exterior surface to the interior surface of body 702 allowing for insertion of a rod 290, 550, 650. The body 702 may also include a first slot 716 extending from the second end 706 of the body 702 to an opening 718 which may be, for example, a round opening, and a second slot 720 extending from a second end 706 of the body 702 to an opening 722 which may be, for example, a round opening. The slots 716, 720 may be positioned between the channel 712 and the opening 714 at the second end 706 of the body 702. Although only two slots 716, 720 are shown, it is also contemplated that additional slots may be included in the tube 700 to allow for expansion of the tube 700 when a fastener 610, 630 is inserted or removed from the tube 700. The interior side of the body 702 may include a groove 724 positioned at the second end 706. The groove 724 may be sized to receive the ridge 670 on the exterior surface of the fasteners 610, 630.

Figure 14:
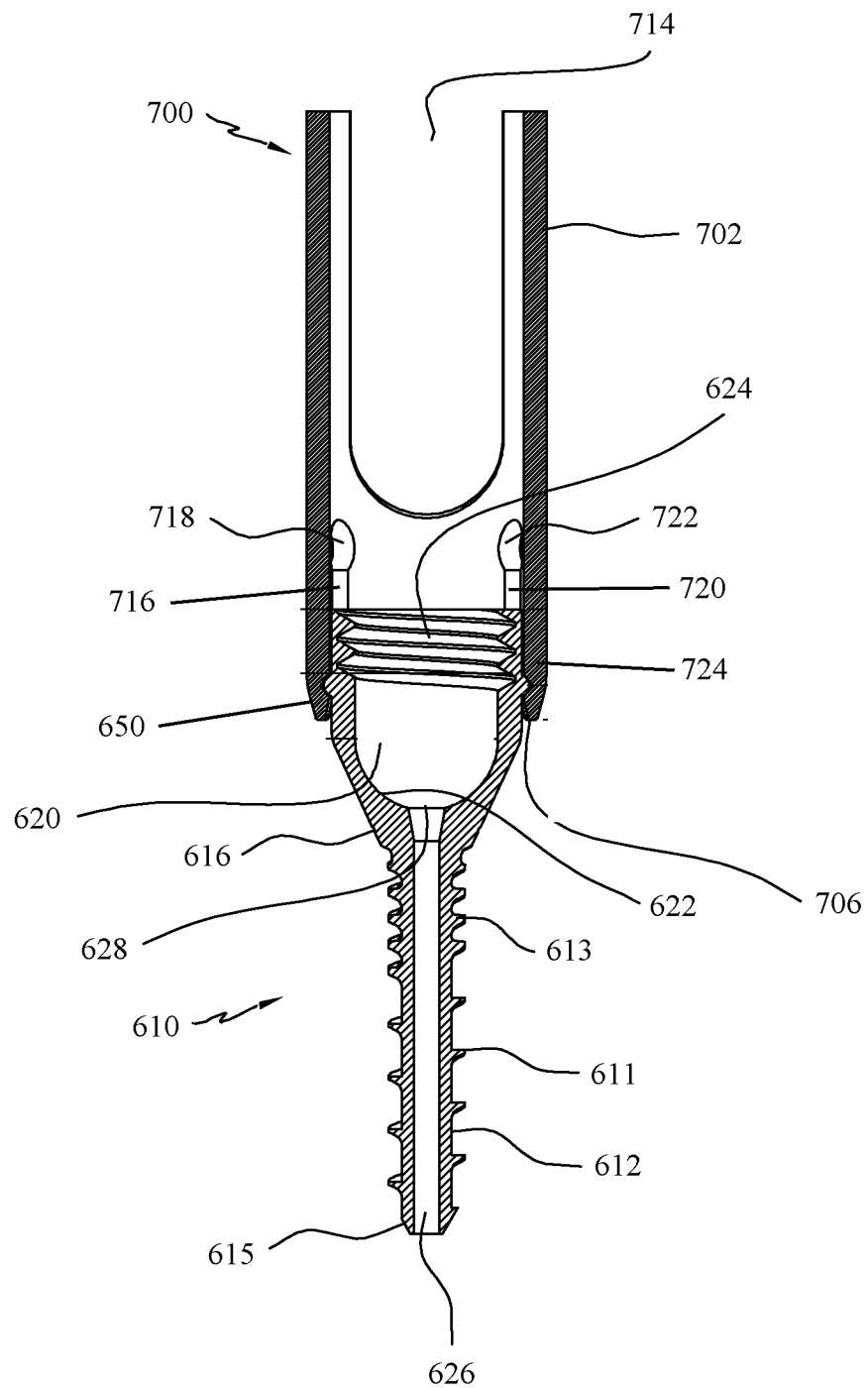
FIG. 14 is a partial, cross-sectional view of a fastener of the fusion system of FIG. 5 coupled to the insertion tower of FIG. 7, in accordance with an aspect of the present invention.

Referring now to FIG. 14, a cross-section of the fastener 610 is shown inserted into an insertion tube 700. To insert the fastener 610 into the tube 700, the first tab 672 may be aligned with the second slot 720 and the second tab 674 may be aligned with the first slot 716. In addition, the opening 620, 640 of the fastener 610, 630 may be aligned with the channel 712 of the tower 700. As the tabs 672, 674 are inserted into the slots 716, 720, the tube 700 will expand to allow the head 614 to be inserted into the central opening 708. The head 614 may be inserted into the central opening 708 until the ridge 670 of the head engages the groove 724 to secure the fastener 610 to the tube 700. To enable the fastener 610 to be secured to the tube 700, the inner diameter of the tube 700 may be, for example, the same dimension as the outer diameter of the head 614 of the fastener 610.

FIGS. 10-13 show the screwdriver 800 which is shaped to engage the fasteners 610, 630 for insertion into a patient. In addition, the screwdriver 800 is sized to be used with the tube 700 and able to be inserted through the central opening 708 of the tube 700. The screwdriver 800 may include a handle portion 810 at a first end 802 of the screwdriver 800 and a shaft portion 820 extending from the handle portion 810 to the second end 804. The handle portion 810 may be positioned generally perpendicular to the shaft portion 820. The handle portion 810 may include a body 812 and an opening 814 for receiving one end of the shaft portion 820. The shaft portion 820 may include a shaft 822 with a screw member 824 at the second end 804 of the screwdriver 800. The screw member 824 may be sized for engaging the opening 628, as shown in FIGS. 6 and 14, of fasteners 610, 630. In addition, the screw member 824 may be sized and shaped to also engage an opening 403 in the set screw 400 to securely tighten the set screw 400 against the rod 650. The screw member 824 may have, for example, a torque, hexagon or any other polygonal shape. The second end 804 of the screwdriver 800 may also include a tab or protrusion 826 for engaging the opening 620 in the fastener 610 to drive the fasteners 610, 630 into a patient's bone. The screwdriver 800 may further include a cannulated opening 828 for receiving a guide wire. The cannulated opening 828 may extend along the shaft 822 to a slot (not shown) in the handle portion 810 which allows the guide wire to be turned into the body 812 of the handle portion 810 to avoid piercing the surgeons gloves.

Referring now to FIG. 15, a portion of the fusion system 600 including the fastener 610, rod 650, and locking cap 400 are shown as partially assembled. To reduce and/or eliminate the incident of axial and rotational motion the radii of the fastener 610, rod 650, and locking cap 400 have been selected to provide a locking fit between the fastener 610, rod 650, and locking cap 400. The rounded end 652 of the rod 650 has a curvature indicated by R1. The base 622 of the head 614 of fastener 610 has a curvature indicated by R2. The recess 408 of the locking cap 400 has a curvature indicated by R3. In one embodiment, for example, the curvature of R1 will be greater than or equal to the curvature of R2 to form an interference fit between the fastener 610 and the rod 650 once secured with the locking cap 400. As described in greater detail above, the ball ends 652, 654 of the rod 650 may have a surface finish that is, for example, rough, nearly knurled, or smooth, to allow for the surface of the ball ends 652, 654 to deform and securely retain the rod 650 within the head 614 of the fastener 610. Further, the curvature R3 of the locking cap 400 may be less than or equal to the curvature of R1 of the rod 650. Where R3 is less than or equal to R1, the locking cap 400 will make contact with the rod 650 near the point where the bottom surface 406 meets the recess 408 and the rod 650 will not make contact with the apex of the recess 408. Therefore, when R3 is less than or equal to R1, there will be a non-contact area gap between the ball end 652 of the rod 650 and the recess 408 of the locking cap 400 to reduce or eliminate the rod 650 from slipping.

Figure 18:
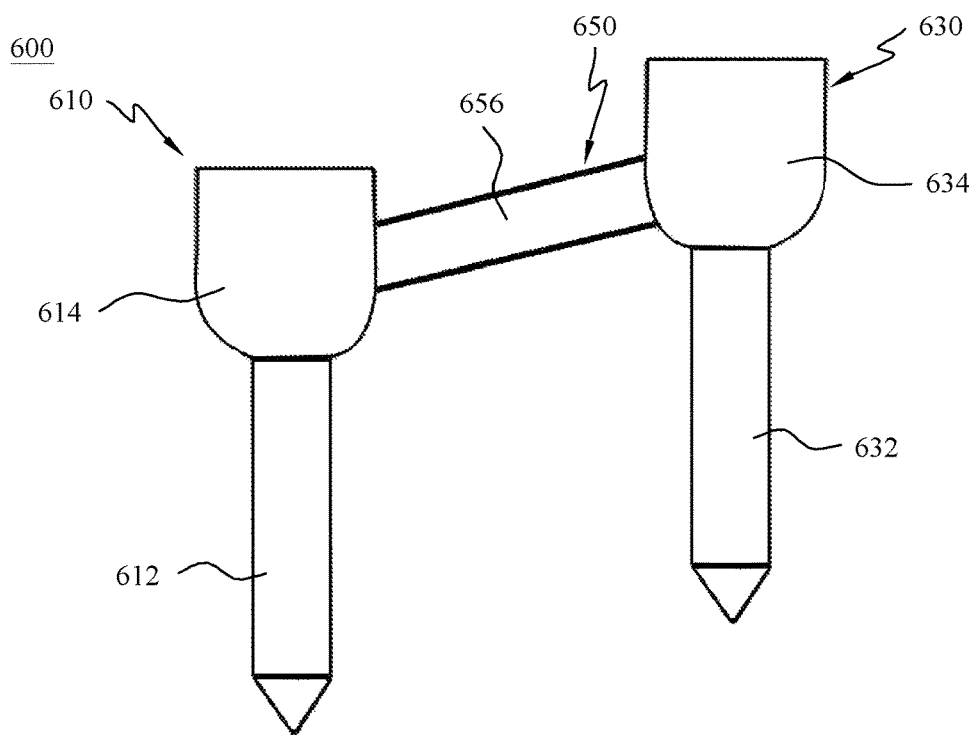
FIG. 18 is a side view the assembled fusion system of FIG. 5 in a first position, in accordance with an aspect of the present invention.
Figure 19:
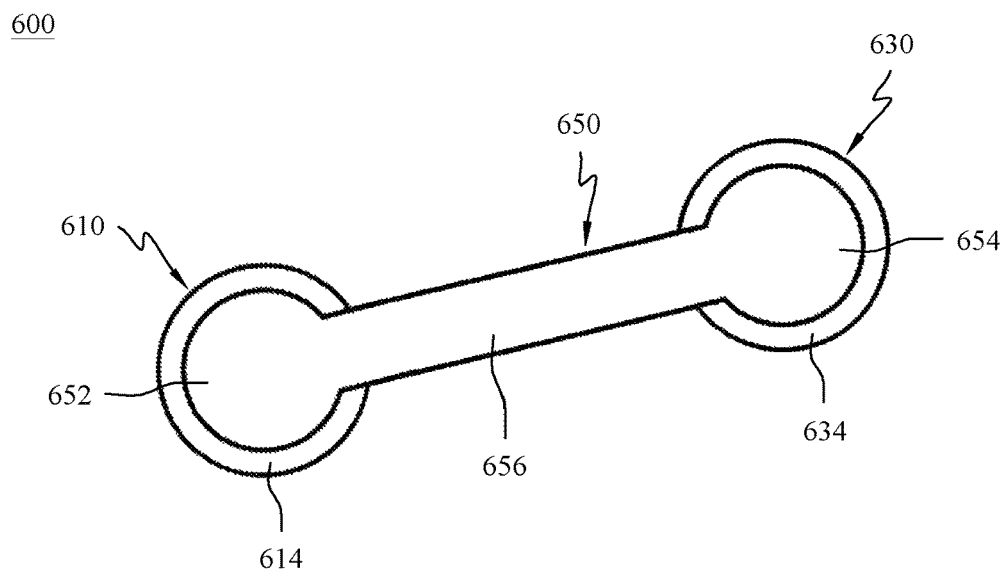
FIG. 19 is a top view of the assembled fusion system of FIG. 5 in a second position, in accordance with an aspect of the present invention.
Figure 20:
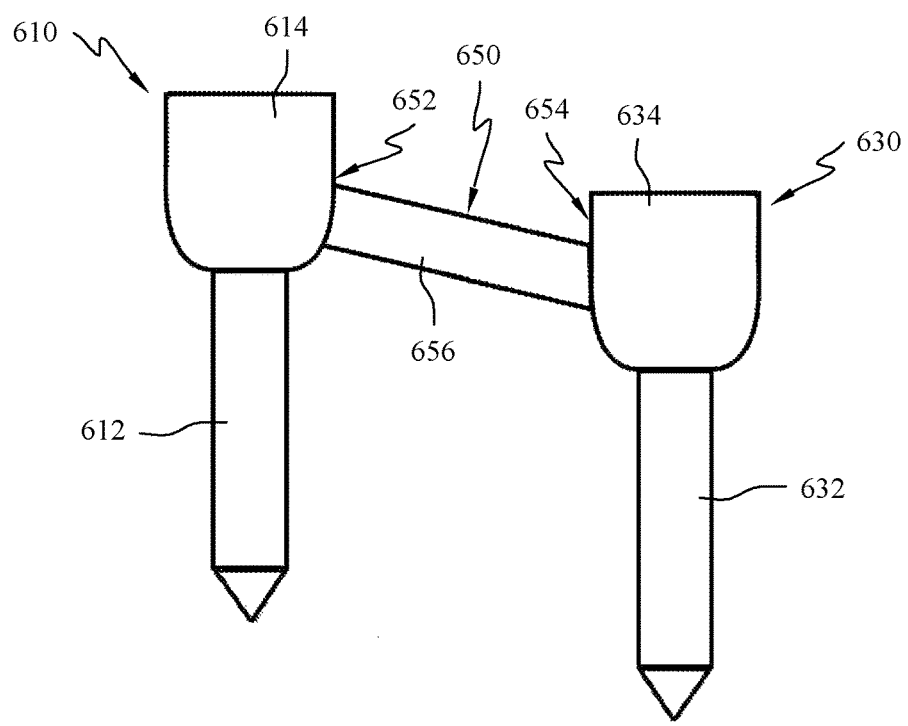
FIG. 20 is a side view of the assembled fusion system of FIG. 5 in a third position, in accordance with an aspect of the present invention.
Figure 21:
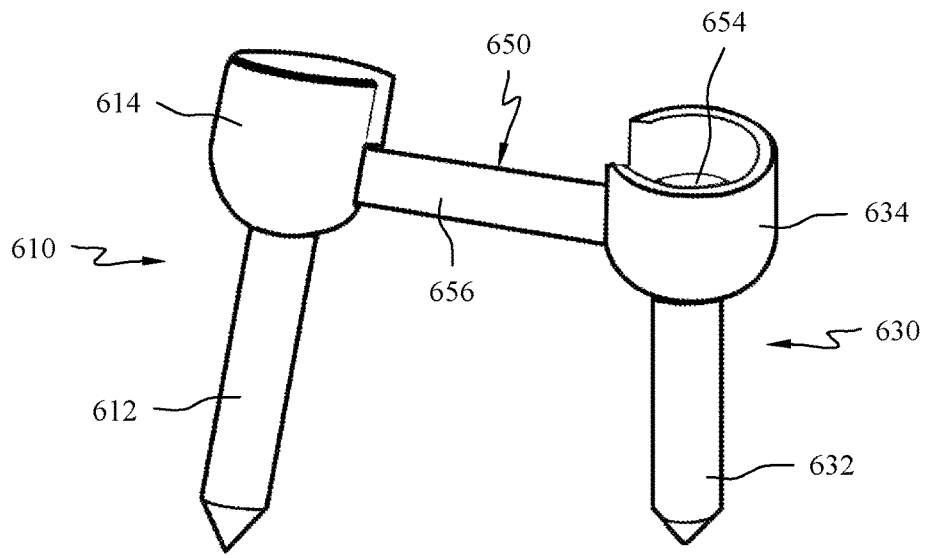
FIG. 21 is a side view of the fusion system of FIG. 5 in a fourth position, in accordance with an aspect of the present invention.

Referring now to FIGS. 18-21, the rod 650 is shown inserted into fasteners 610, 630. In FIG. 18, the rod 650 is positioned angled between the first fastener 610 and the second fastener 630 inserted at varying heights. The second fastener 630 may be positioned, for example, at a greater height than the first fastener 610. Further, FIG. 19 shows the rod 650 positioned angled with respect to the first and second fasteners 610, 630 with the first fastener 610 offset from the second fastener 630. The rod 650 may be positioned angled between the first fastener 610 and second fastener 630 and may be positioned with the first fastener 610 located, for example, at a height greater than the second fastener 630, as shown in FIG. 20. In addition, FIG. 21 shows the first and second fasteners 610, 630 rotated about the long axis of the rod 650 and offset from each other. Once the rod 650 is inserted into the fasteners 610, 630, the load is in compression, tension, or neutral. The load on the rod 650 is perpendicular to the axis of the fasteners 610, 630. As illustrated by FIGS. 18-21, the fasteners 610, 630 are configured to accommodate multi-axial positioning with respect to the rod 650.

A first method for inserting the devices 500, 600 of FIGS. 4-5 into a patient may include cutting a small incision in the patient, for example, a 3 cm incision. Next the fascia is cut and muscles are split in line of the fibers to expose the patient's vertebrae. Once the vertebrae are exposed, an image guidance or fluoroscopy device may be used to insert a first fastener or pedicle screw 510, 610 into a first pedicle of a first vertebra and a second fastener or pedicle screw 530, 630 into an adjacent second pedicle of a second vertebra. The fasteners 510, 610, 530, 630 may be inserted using a guide wire if the fasteners 510, 610, 530, 630 are cannulated or free hand. Then the elongate members 550, 650 may be lowered into the heads 514, 614, 534, 634 of the fasteners 510, 610, 530, 630, respectively. An elongate member 550, 650 that is shorter than the in situ distance between heads 514, 614 and heads 534, 634 may be used for compression of the engaged vertebrae. While an elongate member 550, 650 that is longer than the in situ distance between the heads 514, 614 and heads 534, 634 may be used for distraction of the engaged vertebrae. As the ball ends of the elongate member 550, 650 are inserted into the heads 514, 534, 614, 634 the geometry of the ball ends align with the feature of the fasteners to either compress or distract the construct. As the ball ends are inserted into the heads 514, 534, 614, 634, the elongate member 550, 650 completes the compression or distraction of the bones. A locking mechanism, for example, set screws or locking cap 400 may be inserted into the heads 514, 614, 534, 634 of the first and second fasteners 510, 610, 530, 630 and tightened down to secure the elongate members 550, 650 to the fasteners 510, 610, 530, 630.

Alternatively, the second fastener 530, 630 may be secured to the second end 554, 654 of the elongate member 550, 650 prior to insertion of the second fastener 530, 630 into the second pedicle. Then after insertion of the coupled second fastener 530, 630 and elongate member 550, 650, the elongate member 550, 650 may be lowered into the head 514, 614 of the first fastener 510, 610. The first end 552, 652 of the elongate member 550, 650 is then secured to the first fastener 510, 610. Optionally, additional intermediate fixation devices may be used between the end point fasteners 510, 530, 610, 630. Finally, the patient's incision may be closed.

Another method for inserting the devices 600 of FIG. 5 into a patient may include cutting a small incision in the patient. Next the fascia is cut and muscles are split in line of the fibers to expose the patient's vertebrae, which may be done using dilators. Once the vertebrae are exposed, an insertion system including a tower 700, a fastener 610, 630 and a screwdriver 800 may be assembled for insertion of each of the fasteners 610, 630 into the patient's bone, as described in greater detail above. An image guidance or fluoroscopy device may be used to confirm proper positioning of a first fastener or pedicle screw 610 into a first pedicle of a first vertebra and a second fastener or pedicle screw 630 into an adjacent second pedicle of a second vertebra. The fasteners 610, 630 may optionally be inserted using a guide wire since the fasteners 610, 630 are cannulated or free hand. Once the fasteners 610, 630 are inserted into the vertebrae, the elongate member 650 may be inserted into the heads 614, 634 of the fasteners 610, 630, respectively. An elongate member 650 that is shorter than the in situ distance between head 614 and head 634 may be used for compression of the engaged vertebrae. While an elongate member 650 that is longer than the in situ distance between the head 614 and head 634 may be used for distraction of the engaged vertebrae. As the elongate member 550, 650 is inserted into the heads 514, 534, 614, 634 the force of inserting the elongate member 550, 650 completes the correction of the bones. A locking mechanism, for example, set screws or locking caps 400 may be inserted into the heads 614, 634 of the first and second fasteners 610, 630 and tightened down to secure the elongate member 650 to the fasteners 610, 630. Optionally, additional intermediate fixation devices may be used between the end point fasteners 610, 630. Finally, the patient's incision may be closed.

The elongate members 290, 550, and 650 may have a length. The length of the elongate members 290, 550, and 650 will be selected based on the procedure being performed and whether compression or distraction is desired. For example, a rod that is longer than the position of the in situ fasteners will be used for distraction to move the engaged vertebrae apart and a rod that is shorter than the in situ position of the fasteners will be used for compression to pull the engaged vertebrae together. The length of elongate members 290, 550, and 650 may range from, for example, approximately 10 mm to 60 mm and more specifically approximately 20 mm to 50 mm. The elongate members 290, 550, and 650 may be straight or curved along the longitudinal axis.

The above described methods may be used for surgical procedures including, for example, lumbar, cervical, spinal trauma, pelvic fixation, fracture fixation, bone ends, and the like.

As may be recognized by those of ordinary skill in the art based on the teachings herein, numerous changes and modifications may be made to the above-described and other embodiments of the present invention without departing from the scope of the invention. The fasteners, elongate members, and other components of the devices and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the devices and systems may include more or fewer components or features than the embodiments as described and illustrated herein. For example, the components and features of FIGS. 1-6 may all be used interchangeably and in alternative combinations as would be modified or altered by one of skill in the art. Accordingly, this detailed description of the currently-preferred embodiments is to be taken as illustrative, as opposed to limiting the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiments, the invention is now claimed to be:

1. A fusion system, comprising:
a first fastener comprising a first head with a first slot, a first shaft and a first neck coupling the first head to the first shaft, and wherein the first head comprises a body portion defining an interior surface and a top surface, and a base portion extending below the body portion defining an concave interior surface defined by a first radius, wherein the interior surfaces of the body portion and first base portion of the first head cooperatively forming a first cavity, and wherein the first slot extends through the body portion from the top surface thereof and through a portion of the base portion to the first cavity;
a first locking cap comprising a bottom surface with a concave first recess defined by a second radius, the first locking cap threadably engaged with the body portion of the first head within the first cavity;
a second fastener comprising a second head with a second slot, a second shaft and a second neck coupling the second head to the second shaft, and wherein the second head comprises a body portion defining an interior surface and a top surface, and a base portion extending below the body portion defining a concave interior surface defined by a third radius, wherein the interior surfaces of the body portion and the base portion of the second head cooperatively forming a second cavity, and wherein the second slot extends through the body from the top surface thereof and through a portion of the base portion to the second cavity;
a second locking cap comprising a bottom surface with a concave second recess defined by a fourth radius, the second locking cap threadably engaged with the body portion of the second head within the second cavity; and
an elongate member comprising a first spherical end, a second spherical end, and a coupling shaft extending between the first and second spherical ends,
wherein the first spherical end of the elongate member is secured to the first head of the first fastener within the first cavity via the first locking cap, and the second spherical end of the elongate member is secured to the second head of the second fastener within the second cavity via the second locking cap,
wherein the first spherical end is defined by a fifth radius and includes a diameter that is larger than a diameter of the coupling shaft, and the second spherical end is defined by a sixth radius and includes a diameter that is larger than a diameter of the coupling shaft,
wherein the diameter of the first spherical end is larger than a width of the first slot, and the diameter of the second spherical end is larger than a width of the second slot, and
wherein the fifth radius of the first spherical end is larger than the first radius of the first head and the second radius of the first locking cap, and wherein the sixth radius of the second spherical end is larger than the third radius of the second head and the fourth radius of the second locking cap.

2. The system of claim 1, wherein the first and second fasteners each define an axis, and wherein the first slot extends from top surface of the first head of the first fastener to a position below the mid-point of the first head of the first fastener along the axis thereof, and the second slot extends from the top surface of the second head of the second fastener to a position below the mid-point of the second head of the second fastener along the axis thereof.

3. The system of claim 1, wherein the first locking cap comprises a driver opening on a top surface thereof, and the second locking cap comprises a driver opening on a top surface thereof.

4. The system of claim 1, wherein the first cavity of the first head comprises an opening at the top surface thereof that is in communication with the first slot, and the second cavity of the second head comprises an opening at the top surface thereof that is in communication with the second slot.

5. The system of claim 1, wherein each of the first head and the second head further comprise:
a ridge extending around the circumference of the exterior surface of the body portion;
a first tab positioned on the exterior surface of the body portion and extending from the top surface thereof to the ridge; and a second tab positioned on the exterior surface of the body portion extending from the top surface thereof to the ridge, the second tab being circumferentially spaced apart from the first tab.

6. The system of claim 1, further comprising:
an insertion tower for coupling to at least one of the first fastener and the second fastener; and
a screwdriver sized to engage at least one of the first fastener and the second fastener.

7. The system of claim 6, wherein the insertion tower comprises:
a body with a first end and a second end;
a central opening extending through the body along a longitudinal axis from the first end to the second end;
a channel extending from the second end toward the first end and through the body to the central opening; and
at least one slot extending from the second end toward the first end and positioned spaced apart from and parallel to the channel.

8. The system of claim 7, wherein the at least one slot comprises two slots spaced circumferentially around the body of the insertion tower at the second end.

9. The system of claim 8, wherein at least one of the first head and the second head further comprise a ridge extending around the circumference of the exterior surface of the body portion thereof, and wherein the insertion tower further comprises:
a groove inset into the body of the insertion tower at the second end and sized to receive a ridge on the exterior surface of at least one of the first fastener and the second fastener.

10. The system of claim 6, wherein the screwdriver comprises:
a handle portion; and
a shaft portion coupled to a central part of the handle portion, wherein the handle portion is perpendicular to the shaft portion.

11. The system of claim 10, wherein the shaft portion of the screwdriver comprises:
a shaft with a first end and a second end;
a screw member positioned at the second end for engaging at least one of the first fastener and the second fastener;
a protrusion for engaging a second opening of at least one of the first fastener and the second fastener.

12. A method of assembling a fusion system, comprising:
obtaining a first tower, a second tower, and the fusion system of claim 1;
coupling the first fastener of the fusion system to the first tower;
coupling the second fastener of the fusion system to the second tower;
inserting the first spherical end of the elongate member into the first cavity of the first fastener;
inserting the second spherical end of the elongate member into the second cavity of the second fastener;
engaging the first locking cap with a screwdriver;
screwing the first locking cap into the first cavity of the first head of the first fastener to secure the first spherical end of the elongate member to the first fastener;
engaging the second locking cap with a screwdriver; and
screwing the second locking cap into the second cavity of the second head of the second fastener to secure the second spherical end of the elongate member to the second fastener.

13. The method of claim 12, further comprising:
removing the first tower from the first fastener; and
removing the second tower from the second fastener.

14. A surgical method for inserting a fusion system, comprising:
exposing a patient's vertebrae;
obtaining the fusion system of claim 1;
inserting the first fastener of the fusion system into a first vertebra of the patient's vertebrae;
inserting the second fastener of the fusion system into a second vertebra adjacent to the first vertebra of the patient's vertebrae; and
coupling the first fastener and second fastener together via the elongate member of the fusion system.

15. The method of claim 14, wherein the fusion system further comprises:
at least one insertion tower for coupling to at least one of the first fastener and the second fastener; and
at least one screwdriver for coupling to at least one of the first fastener, the second fastener, the first locking cap, and the second locking cap.

16. The method of claim 15, wherein at least one of the first head and the second head further comprise a ridge extending around the circumference of the exterior surface of the body portion thereof, and wherein the at least one insertion tower comprises:
a body with a first end and a second end;
a central opening extending through the body along a longitudinal axis from the first end to the second end;
a channel extending from the second end toward the first end and through the body to the central opening;
at least one slot extending from the second end toward the first end and positioned spaced apart from and parallel to the channel; and
a groove inset into the body of the insertion tower at the second end and sized to receive the ridge of at least one of the first fastener and the second fastener; and
wherein the at least one screwdriver comprises:
a handle portion; and
a shaft portion coupled to a central part of the handle portion, wherein the handle portion is perpendicular to the shaft portion, the shaft portion comprising:
a shaft with a first end and a second end;
a screw member positioned at the second end for engaging at least one of the first fastener and the second fastener;
a protrusion for engaging a second opening of at least one of the first fastener and the second fastener.

17. The method of claim 16, wherein inserting the first fastener into the first vertebra comprises:
coupling the first fastener to the second end of the at least one insertion tube;
inserting the screw member and the protrusion of the at least one screwdriver into the first cavity of the first head of the first fastener; and
rotating the screwdriver to drive the first fastener into the first vertebra.

18. The method of claim 17, wherein inserting the second fastener into the second vertebra comprises:
coupling the second fastener to the second end of the at least one insertion tube;
inserting the screw member and the protrusion of the at least one screwdriver into the second cavity of the second head of the second fastener; and
rotating the screwdriver to drive the second fastener into the second vertebra.

19. The method of claim 18, wherein coupling the first fastener and the second fastener together via the elongate member of the fusion system comprises:
  inserting the first spherical end of the elongate member into the first cavity of the first head of the first fastener;
  screwing the first locking cap into the first cavity of the first head of the first fastener to secure the first spherical end of the elongate member between the concave interior surface of the first head of the first fastener and the concave first recess of the bottom surface of the first locking cap;
  inserting the second spherical end of the elongate member into the second cavity of the second head of the second fastener; and
  screwing the second locking cap into the second cavity of the second head of the second fastener to secure the second spherical end of the elongate member between the concave interior surface of the second head of the second fastener and the concave second recess of the bottom surface of the second locking cap.

20. The method of claim 19, wherein coupling the first fastener and the second fastener together via the elongate member may moves the first fastener and the second fastener with respect to each other, and wherein the movement of the first and second with respect to each other adds compression forces, maintains compression forces, adds distraction forces, or maintains distraction forces between the first and second vertebra.

21. The system of claim 1, wherein the first fastener is elongated along a first axis and the second fastener is elongated along a second axis, wherein a first bottom end surface of the first slot defined by the base portion of the first head is positioned below the center of the first spherical end of the elongate member along the first axis, and wherein a second bottom end surface of the second slot defined by the base portion of the second head is positioned below the center of the second spherical end of the elongate member along the second axis.

22. The system of claim 21, wherein the first slot is configured to provide for angulation of the elongate member within the first cavity along a first axial plane that is aligned with the first axis between the first bottom end surface and the top surface of the first head with the range of 20 degrees to 40 degrees, and wherein the second slot is configured to provide for angulation of the elongate member within the second cavity along a second axial plane that is aligned with the second axis between the second bottom end surface and the top surface of the second head with the range of 20 degrees to 40 degrees.

23. The system of claim 22, wherein the first slot is configured to provide for angulation of the elongate member within the first cavity along a first rotational plane that is normal with respect to the first axis between opposing lateral sides of the first slot of the first head with the range of 10 degrees to 30 degrees, and wherein the second slot is configured to provide for angulation of the elongate member within the second cavity along a second rotational plane that is normal with respect to the second axis between opposing lateral sides of the second slot of the second head with the range of 10 degrees to 30 degrees.

24. The system of claim 1, wherein the first fastener is elongated along a first axis and the second fastener is elongated along a second axis, and wherein the body portion of the first head is annular and extends continuously circumferentially about the first axis between opposing lateral sides of the first slot, and the body portion of the second head is annular and extends continuously circumferentially about the second axis between opposing lateral sides of the second slot.

25. The system of claim 24, wherein the body portion of the first head extends circumferentially about the first axis between opposing lateral sides of the first slot within the range of greater than 180 degrees and less than 345 degrees, and the body portion of the second head extends circumferentially about the second axis between opposing lateral sides of the second slot within the range of greater than 180 degrees and less than 345 degrees.

26. A fusion system, comprising:
  a rod comprising a first spherical end, a second spherical end, and a shaft portion extending between the first and second spherical ends;
  a first one piece screw that accommodates multi-axial positioning of the rod with respect to the first one piece screw, comprising a first head with a first slot, a first shaft and a first neck coupling the first head to the first shaft, wherein the first head comprises:
    a body portion defining an annular interior surface and a top surface; and
    a base portion extending below the body portion defining an concave interior surface defined by a first radius,
    wherein the interior surfaces of the body portion and first base portion of the first head cooperatively form a first cavity, and
    wherein the first slot extends through the body portion from the top surface thereof and through a portion of the base portion to the first cavity;
  a second one piece screw that accommodates multi-axial positioning of the rod with respect to the second one piece screw, comprising a second head with a second slot, a second shaft and a second neck coupling the second head to the second shaft, wherein the second head comprises:
    a body portion defining an annular interior surface and a top surface; and
    a base portion extending below the body portion defining an concave interior surface defined by a third radius,
    wherein the interior surfaces of the body portion and the base portion of the second head cooperatively form a second cavity, and
    wherein the second slot extends through the body from the top surface thereof and through a portion of the base portion to the second cavity;
  a first locking cap with a driver opening on a top surface and a bottom surface with an concave first recess defined by a second radius, the first locking cap threadably engaged with the body portion of the first head within the first cavity to couple the first spherical end of the rod within the first cavity; and
  a second locking cap with a driver opening on a top surface and a bottom surface with an concave second recess defined by a fourth radius, the second locking cap threadably engaged with the body portion of the second head within the second cavity to couple the second spherical end of the rod within the second cavity,
  wherein the first spherical end is defined by a fifth radius and includes a diameter that is larger than a diameter of the shaft portion, and the second spherical end is defined by a sixth radius and includes a diameter that is larger than a diameter of the shaft portion, wherein the diameter of the first spherical end is larger than a width of the first slot, and the diameter of the second spherical end is larger than a width of the second slot, wherein the fifth radius of the first spherical end is larger than the first radius of the first head and the second radius of the first locking cap, and wherein the sixth radius of the second spherical end is larger than the third radius of the second head and the fourth radius of the second locking cap, wherein the first one piece screw is elongated along a first axis and the second one piece screw is elongated along a second axis, wherein a first bottom end surface of the first slot defined by the base portion of the first head is positioned below the center of the first spherical end of the rod along the first axis, and wherein a second bottom end surface of the second slot defined by the base portion of the second head is positioned below the center of the second spherical end of the rod along the second axis.

27. The system of claim 26, wherein the first slot is configured to provide for angulation of the rod within the first cavity along a first axial plane that is aligned with the first axis between the first bottom end surface and the top surface of the first head with the range of 20 degrees to 40 degrees, and wherein the second slot is configured to provide for angulation of the rod within the second cavity along a second axial plane that is aligned with the second axis between the second bottom end surface and the top surface of the second head with the range of 20 degrees to 40 degrees.

28. The system of claim 27, wherein the first slot is configured to provide for angulation of the rod within the first cavity along a first rotational plane that is normal with respect to the first axis between opposing lateral sides of the first slot of the first head with the range of 10 degrees to 30 degrees, and wherein the second slot is configured to provide for angulation of the rod within the second cavity along a second rotational plane that is normal with respect to the second axis between opposing lateral sides of the second slot of the second head with the range of 10 degrees to 30 degrees.

* * * * *

UNITED STATES PATENT AND TRADEMARK OFFICE
CERTIFICATE OF CORRECTION

PATENT NO.           : 10,368,914 B2                                        Page 1 of 1
APPLICATION NO.      : 15/463726
DATED                : August 6, 2019
INVENTOR(S)          : Serbousek et al.

It is certified that error appears in the above-identified patent and that said Letters Patent is hereby corrected as shown below:

In the Claims

Column 15, Line 24: Claim 20, Delete "member may moves" and insert -- member moves --

Signed and Sealed this
Twenty-fourth Day of September, 2019

Andrei Iancu
*Director of the United States Patent and Trademark Office*